(12) United States Patent
Fletcher-Heath et al.

(10) Patent No.: US 7,329,890 B2
(45) Date of Patent: Feb. 12, 2008

(54) COMPUTED RADIOGRAPHY CASSETTE SYSTEM

(75) Inventors: Lynn M. Fletcher-Heath, Rochester, NY (US); Francisca Sugiro, Spencerport, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 96 days.

(21) Appl. No.: 11/230,121

(22) Filed: Sep. 19, 2005

(65) Prior Publication Data

US 2007/0018125 A1     Jan. 25, 2007

Related U.S. Application Data

(60) Provisional application No. 60/701,667, filed on Jul. 22, 2005.

(51) Int. Cl.
*G03B 42/02* (2006.01)
(52) U.S. Cl. .......................... 250/581; 250/584
(58) Field of Classification Search ................ 250/584; 235/375, 462.01, 462.05, 462.13, 462.15, 235/462.45, 472.01
See application file for complete search history.

(56) References Cited

U.S. PATENT DOCUMENTS

| | | | |
|---|---|---|---|
| 1,164,987 A | 12/1915 | Bucky | |
| 4,960,994 A | 10/1990 | Muller et al. | |
| 5,008,920 A | 4/1991 | Gralak | |
| 5,027,274 A | 6/1991 | Takayanagi | |
| 5,264,684 A | 11/1993 | Weil | |
| 5,334,851 A | 8/1994 | Good et al. | |
| 5,376,806 A * | 12/1994 | Hejazi | 250/584 |
| 5,418,355 A | 5/1995 | Weil | |
| 5,592,374 A | 1/1997 | Fellegara et al. | |
| 5,627,381 A * | 5/1997 | Kulpinski | 250/588 |
| 5,646,416 A | 7/1997 | Van de Velde | |
| 5,661,818 A | 8/1997 | Gaborski et al. | |
| 5,757,021 A | 5/1998 | Dewaele | |
| 5,978,518 A | 11/1999 | Oliyide et al. | |
| 6,069,979 A | 5/2000 | VanMetter | |
| 6,269,176 B1 | 7/2001 | Barski et al. | |
| 6,271,536 B1 | 8/2001 | Buytaert et al. | |
| 6,359,628 B1 | 3/2002 | Buytaert | |
| 6,379,044 B1 | 4/2002 | Vastenaeken et al. | |

* cited by examiner

*Primary Examiner*—David Porta
*Assistant Examiner*—Mark R Gaworecki (57) ABSTRACT

A method for scanning and processing computed radiography x-ray images in order to maximize the usage of cassette options. The storage phosphor radiography imaging method of the invention employs a cassette comprising a storage phosphor screen adapted to be exposed to x-rays to store a latent x-ray image in the screen and read using a reader. The method includes the steps of: associating cassette information with the cassette using an identification member affixed to the cassette or storage phosphor screen, the cassette information comprising information relating to characteristics of the cassette relevant to the reading of the screen by the reader; prior to reading the exposed storage phosphor screen to generate a digital image signal, scanning the identification member to obtain the cassette information; and reading the exposed storage phosphor screen in accordance with the cassette information to generate the digital image signal.

13 Claims, 6 Drawing Sheets

COMPUTED RADIOGRAPHY CASSETTE SYSTEM

CROSS REFERENCE TO RELATED APPLICATIONS

Reference is made to, and priority is claimed from, Provisional Patent Application No. 60/701,667 entitled "COMPUTED RADIOGRAPHY CASSETTE SYSTEM", filed on Jul. 22, 2005 in the names of Fletcher-Heath et al., and which is assigned to the assignee of this application.

FIELD OF THE INVENTION

The present invention relates to an image processing apparatus for capturing an image signal, representing a diagnostic image, acquired under conditions relevant for pre-specified radiographic imaging applications.

BACKGROUND OF THE INVENTION

Radiography refers to a general system, or modality, for recording a radiation image from the transmission of X-rays through the body of a patient. Conventional radiography uses a film/screen combination as the capture device. Such a film/screen can be digitized to produce a digital image. Digital radiography may use either a flat-panel detector (DR) or stimulable phosphor plates (CR). For either digital radiography technology, the output digital signal is usually converted into a unit that is linear with the logarithm of incident exposure. Digital systems can record radiation exposure over a very wide dynamic range, typically on the order of 10,000:1, so that exposure error is seldom a problem.

Due to the wide dynamic range of digital radiography, the raw digital signal produced by the modality will need to be enhanced to produce a visible image suitable for diagnosis by a medical clinician. Image enhancement techniques typically manipulate the spatial frequency components of the image, in order to sharpen edges and to increase the local contrast, and create a tonescale curve, in order to render a visible image with sufficient global contrast.

Algorithms designed to implement an enhancement strategy are usually parameterized by a set of image processing conditions that describe the details of the strategy. Such conditions can specify which spatial frequencies are to be modified, to what degree, and the like. Various image processing algorithms are known to those skilled in the art. For example, refer to U.S. Pat. No. 5,978,518 (Oliyide) and U.S. Pat. No. 6,069,979 (VanMetter).

Image processing, however, is not fully responsible for the quality of the presented image. The precursor to a well-rendered image is a proper acquisition. Example requirements for a properly acquired image are: proper alignment and distance of the X-ray source to the acquisition device, proper technique factors for the body part being imaged (kVp, mAs), minimal scatter which can be mitigated by proper use of collimation and scatter-reduction grids, high resolution acquisition devices when warranted, etc. The present invention addresses the need to have a variety of available acquisition choices including anti-scatter grids and image resolution based on exam type.

The use of grids has been recommended for X-ray radiography when Gustave Bucky introduced the first stationary grid for scatter reduction yielding image contrast improvement. Refer to U.S. Pat. No. 1,164,987 (Bucky) which issued in 1915. Accordingly, these devices are commonly found in most radiology departments and available in many configurations.

A grid typically includes of a series of lead foil strips separated by X-ray-transmissive spacers. The spacing of the strips determines the grid frequency, and the height-to-distance ratio determines to grid ratio. Grids can be oriented horizontally or vertically. Two general methods of use exist for grids: stationary and moving. With stationary grids, grid lines will leave shadows in the radiographic image. With a moving grid, the grid lines are intentionally blurred out by the motion.

In the case of stationary grid lines, the high frequency grid pattern, in combination with the scanning frequency of the scanning system, may cause an image artifact viewable on a soft copy display. This is caused by aliasing, which is introduced by the discrete sampling of the high frequency lead strips in the image by the scanning system. Grid suppression algorithms are known. For example, refer to U.S. Pat. No. 6,269,176 (Barski), commonly assigned. Such a suppression algorithm may be used to isolate and suppress this artifact. Also, if a moving grid system is rendered inoperable, stationary lines will be imaged in the latent image and a grid detection method such as in U.S. Pat. No. 5,661,818 (Gaborski) issued Aug. 26, 1997 and the above mentioned grid suppression algorithm could be of interest.

Optional grid detection and suppression is situation dependent. In the situation of a cassette with an imbedded grid, as in U.S. Pat. No. 5,008,920 (Gralak) issued Apr. 16, 1991, detection may not be desired if the grid resolution is specified.

Image resolution is another optional acquisition characteristic, and, for computed radiography (CR) which employs storage phosphor, is dependent upon the cassette phosphor and the capabilities of the CR scanning device. A cassette having a high-resolution phosphor may be read on a CR scanner with more than one scanning speed or laser characteristic (i.e. power, spot size, and the like). Applicants have recognized that a method or user interface to choose these available options can be used to indicate the anticipated scan sequence.

A component to image quality as influenced by acquisition is CR scanner calibration. Calibration is necessary for adjusting the differences in machine hardware and setup. By adjusting for variances, a calibration profile will give the same quality images on each machine when calibrated correctly. The goal of the calibration is to expose a plate to a uniform exposure and adjust each gain so the value read from the plate are not only uniform but of a value equal or close to the actual exposure of the plate. Choosing this correctly can have an impact on the contrast to noise characteristics of a low exposure image.

The use of identification codes on cassettes is known, such as described in U.S. Pat. No. 4,960,994 (Muller) issued on Oct. 2, 1990, U.S. Pat. No. 5,264,684 (Weil) issued Nov. 23, 1993, U.S. Pat. No. 5,334,851 (Good) issued Aug. 2, 1994, U.S. Pat. No. 5,418,355 (Weil) issued May 23, 1995, U.S. Pat. No. 5,592,374 (Fellegara) issued Jan. 7, 1997, U.S. Pat. No. 5,646,416 (VandeVelde) issued Jul. 8, 1997, U.S. Pat. No. 5,757,021 (Dewaele) issued May 26, 1998, and U.S. Pat. No. 6,379,044 (Vastenacken) issued Apr. 30, 2002. Identification codes are used to: identify patients; identify phosphor screen; identify image particulars such as body part, X-ray exposure conditions, and technique deviations from expected exposures; link patients with their image data; and control aspects of acquisition.

U.S. Pat. No. 5,027,274 (Takayanagi) issued Jun. 25, 1991, describes a management system to link and handle CR image data, a patient identification photograph and technique information. However, there is no control of the CR scanner.

The use of radio frequency tags for CR applications is known, for example, see U.S. Pat. No. 6,271,536 (Buytaert) issued Aug. 7, 2001 and U.S. Pat. No. 6,359,628 (Buytaert) issued Mar. 19, 2002, which are directed to a radiographic image identification method including an radio frequency tag.

Accordingly, there exists a need for an apparatus and method where post-acquisition options, such as scanning speeds, system calibration, various grid options and processing algorithms, are available.

The present invention addresses the need for flexibility in the current CR market, where post-acquisition options, such as scanning speeds, system calibration, various grid options and processing algorithms, are available.

SUMMARY OF THE INVENTION

An object of the present invention is to provide a method wherein post-acquisition options, such as scanning speeds, system calibration, various grid options and processing algorithms, can be employed.

Another object of the present invention is to a provide a method for exercising scanning and processing options with minimal modifications to the current system.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

The present invention allows the scanning and processing of raw digital X-ray image signals for presentation to a clinician to enable maximal visual diagnostic information to be conveyed.

According to the present invention, the image acquisition apparatus comprises an X-ray imaging modality, a coded X-ray receiving plate, a cassette scanner with switchable resolution and calibration capabilities, image processing algorithms, an acquisition workstation and a display workstation.

The present invention provides a light-weight apparatus for acquisition of CR radiographic exams with a means for switching between scanning and processing techniques. The present invention provides a mechanism for applying options such as self-contained scatter reducing hardware and compensation software, gain adjustments on the CR reader reducing allowable exposure, increased scan resolution and various image processing algorithms designated by the cassette instead of the exam type.

According to one aspect of the present invention, there is provided a storage phosphor radiography imaging method that employs a cassette comprising a storage phosphor screen adapted to be exposed to x-rays to store a latent x-ray image in the screen and read using a reader. The method comprises the steps of: associating cassette information with the cassette using an identification member affixed to the cassette or storage phosphor screen, the cassette information comprising information relating to characteristics of the cassette relevant to the reading of the screen by the reader; prior to reading the exposed storage phosphor screen to generate a digital image signal, scanning the identification member to obtain the cassette information; and reading the exposed storage phosphor screen in accordance with the cassette information to generate the digital image signal.

According to another aspect of the present invention, there is provided a storage phosphor radiography imaging method that employs a cassette comprising a storage phosphor screen adapted to be exposed to x-rays to store a latent x-ray image in the screen. The cassette comprising the screen is provided. The cassette includes an identification member affixed thereto wherein cassette code information is associated with the identification member. The cassette code information comprising information relating to characteristics of the cassette relevant to reading of the screen by a reader to generate a digital image signal and comprising characteristics of the cassette relevant to processing of the generated digital image signal. A scanning member is provided which is adapted to scan the identification member to obtain the cassette code information. After obtaining the cassette code information, the exposed storage phosphor screen is read by the reader in accordance with the cassette code information to generate the digital image signal. Processing of the digital image signal is then accomplished in accordance with the cassette code information.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE PREFERRED EMBODIMENTS

The following is a detailed description of the preferred embodiments of the invention, reference being made to the drawings in which the same reference numerals identify the same elements of structure in each of the several figures.

Figure 1A:
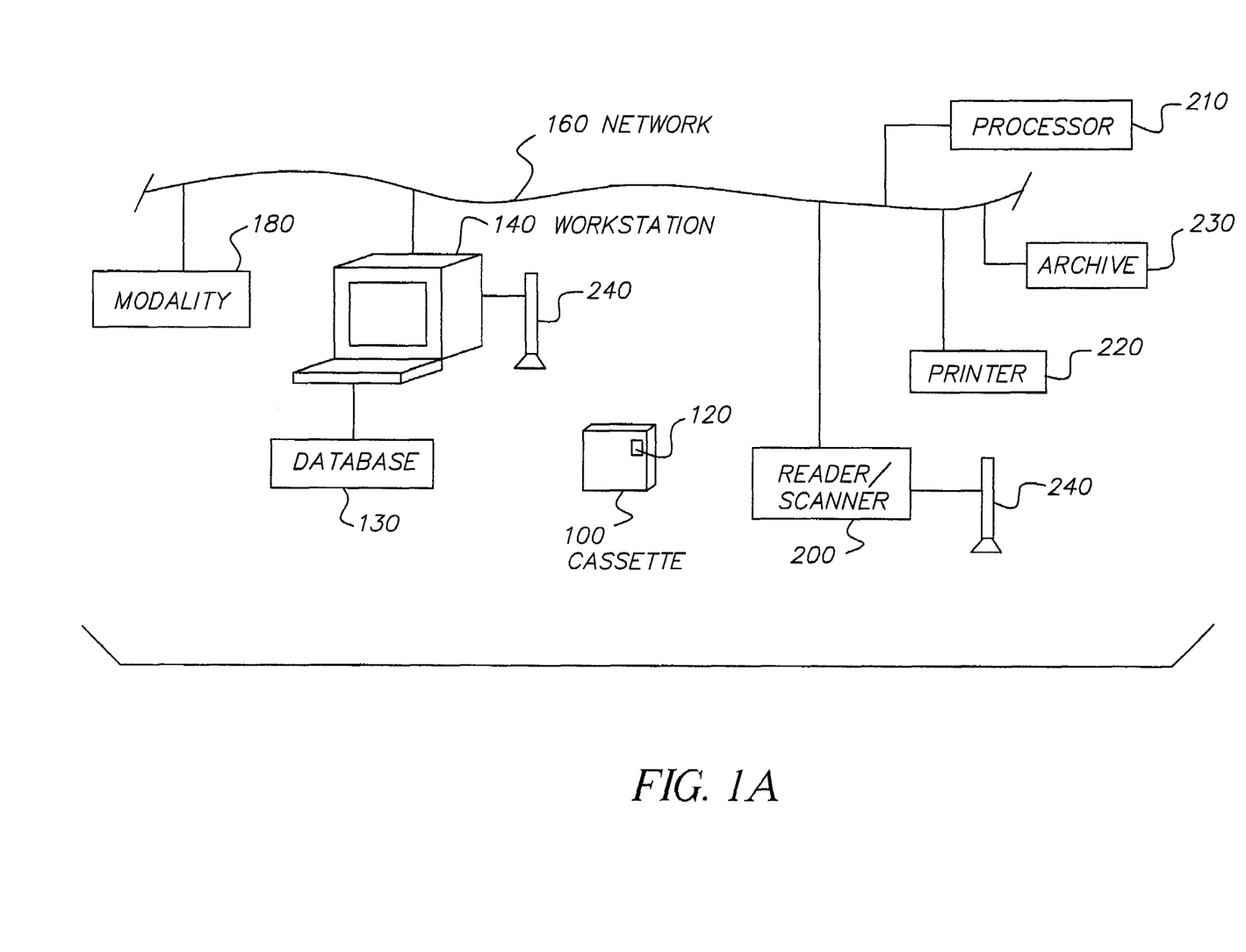
FIG. 1A schematically shows a radiography system in accordance with the present invention.

FIG. 1A schematically shows a radiography system in accordance with the present invention wherein a radiographic image is recorded on a storage phosphor screen. The storage phosphor screen is disposed within a cassette 100. A cassette code/information is associated with cassette 100. Means are provided on cassette 100 for identifying the cassette or the cassette code.

For example, the code can be directly stored in an id member 120 affixed to or disposed within cassette 100. Id member 120 can be a bar code or a radio frequency tag or the like. Id member 120 would store the particular information which would be employed by the system, as will be more particularly described below.

Alternatively, the code can be obtained indirectly using id member 120. That is, the id member 120 can be a pointer/marker to a database 130 (such as stored on a workstation 140), wherein id member 120 is associated with the code. For example, id member 120 might indicate refer to "code X" in a database, wherein "code X" would comprise particular information.

Workstation 140 can be a preview station or computer or the like. Workstation 140 can be networked by means of network 160 to one or more modalities 180. A computed radiography reader/scanner 200 is provided for reading the exposed storage phosphor screen disposed within cassette 10. A processor 210 is provided for conducting image processing on the image read by reader 200. Both reader 200 and processor 210 can be in communication with network 160. A printer 220, such as laser printer, can also be provided to generate a hardcopy of an image processed by processor 210. An archive 230 may be in communication with network 160 for storing data.

Workstation 140 is provided with a device 240 for reading the information disposed in id member 120. Alternatively, for example if id member 120 is a radio frequency tag, device 240 can be a read/write device for reading the information and writing new/different information to the id member. Device 240 can also be provided with reader 200.

While FIG. 1A shows the element being networked, it is noted that the elements can be directly connected or routed to combinations of other destinations, such as the printer and archives.

Figure 1B:
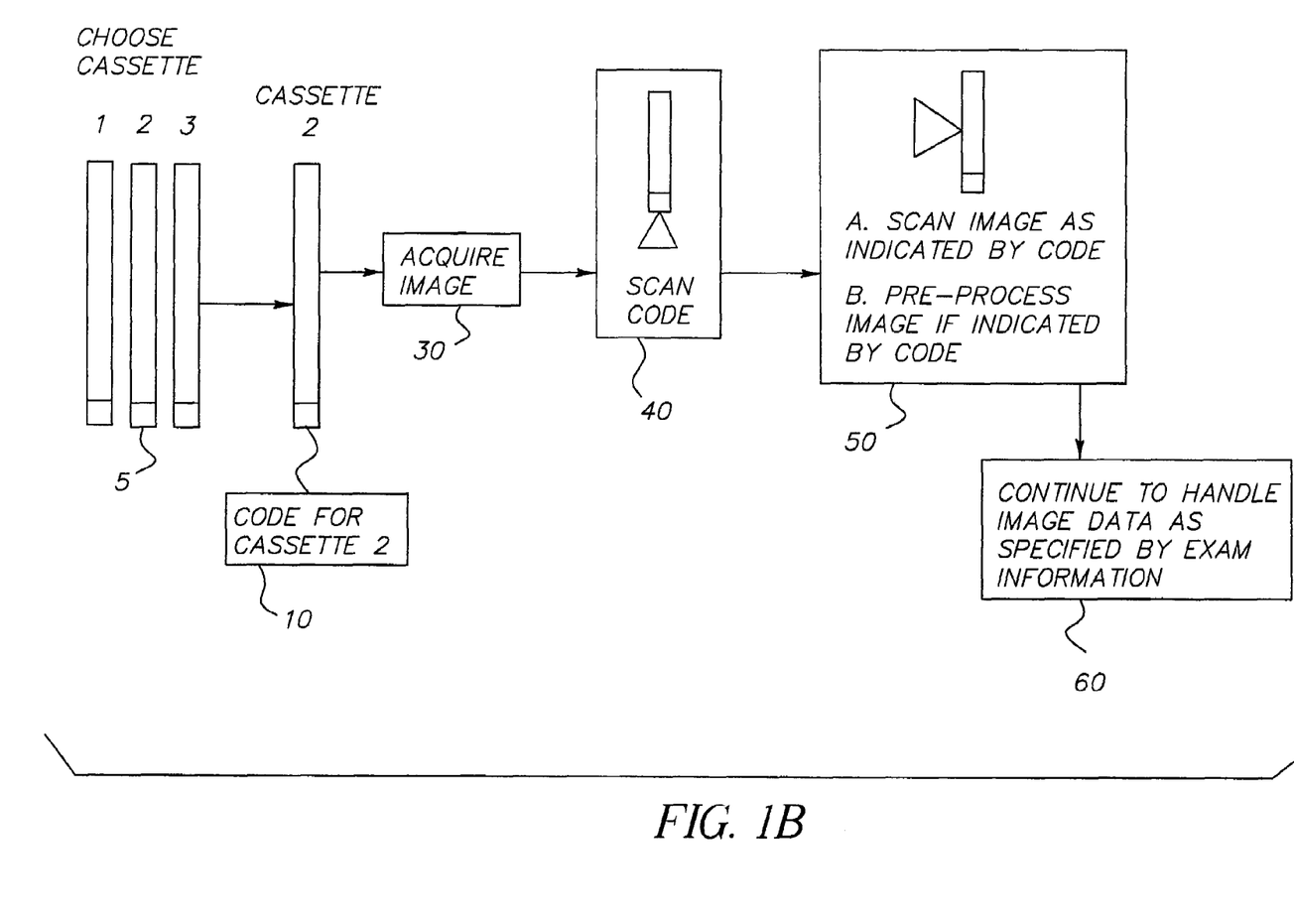
FIG. 1B shows a diagrammatic illustration of the use of the coded cassette and the subsequent scanner interaction in accordance with the present invention.

FIG. 1B generally illustrates the method of the present invention using the system shown in FIG. 1A. More particularly, FIG. 1B shows a diagrammatic illustration of the use of the coded cassette and the subsequent scanner interaction in accordance with the present invention.

Using the CR cassette system of the present invention, a user selects/chooses a cassette based on the type of image that is to be acquired (shown at block 5). The selected cassette includes a special scannable code associating the reading/scanning procedure with the cassette type (shown at block 10). As indicated above, the code can be disposed in id member 120 or obtained by database 130.

The image is acquired using proper computed radiography techniques (shown at block 30) using modality 180.

Referring now to block 40, once the image is acquired (i.e., the storage phosphor screen is exposed), device 240 can be used to scan id member 120 and determine the code associated with selected cassette.

The code includes information about the image and/or cassette relevant to the reading/scanning of the exposed screen by reader 200. For example, a grid can be disposed within cassette 100, attached to cassette 100, otherwise associated with cassette 100, or absent from cassette 100. For example, the cassette code can include information about the type of grid and/or the scanning characteristics which should be employed since a particular type of grid was used (or absent from) the cassette. For example, information which would affect a change in the pixel matrix size.

The code can also include information about further image processing of the scanned image. That is, any image processing that might be applied to the image by processor 210 once the image is read/scanned by reader 200.

Other information that can be included in the cassette code includes information regarding:

laser spot size (for example, 100 or 60 micron)

laser spot shape (for example, round or elliptical, and the like)

laser power (for example, 3, 7, 15, 30, 60 mW)

variable sampling clock for frequency (e.g., can be set by the PMT board, frequency examples are 300 kHz and 600 kHz)

enable and disable collector profile correction for calibration enable/disable recalibration (for example, reload electronic gain setting without recalibration, e.g., 1×, 5×, or 10×)

variable PMT gain (for example, 900, 800, 700, 600, and 500 volts)

ability to enable/disable fast scan filter ability to change the DC level of the electronics signal ability to turn on/off the laser for scanning variable or differing galvo speed variable slow scan sampling pitch variable pixel size (for example, 100, and 50 micron)

variable pixel matrix size exposure level patient size body part and/or projection grid (use or not use)

grid characteristics (for example, resolution, orientation, focus range, thickness, lead content, ratio, and the like)

screen characteristics (for example, phosphor type, thickness, age, flexibility, backing, and the like)

portable vs. ambulatory cassette type (for example, light-weight, regular, and the like)

Using the cassette code, reader 200 can read the image in accordance with the code (block 50, step A).

The cassette code might indicate that the image requires particular pre-processing (block 50, step B). At block 60, the architecture passes the data along to the designated CR image processing software (processor 210).

The X-ray imaging modality 18 used to acquire the image (referenced in at block 30) is typically either a CR or a DR imaging device.

Figure 2A:
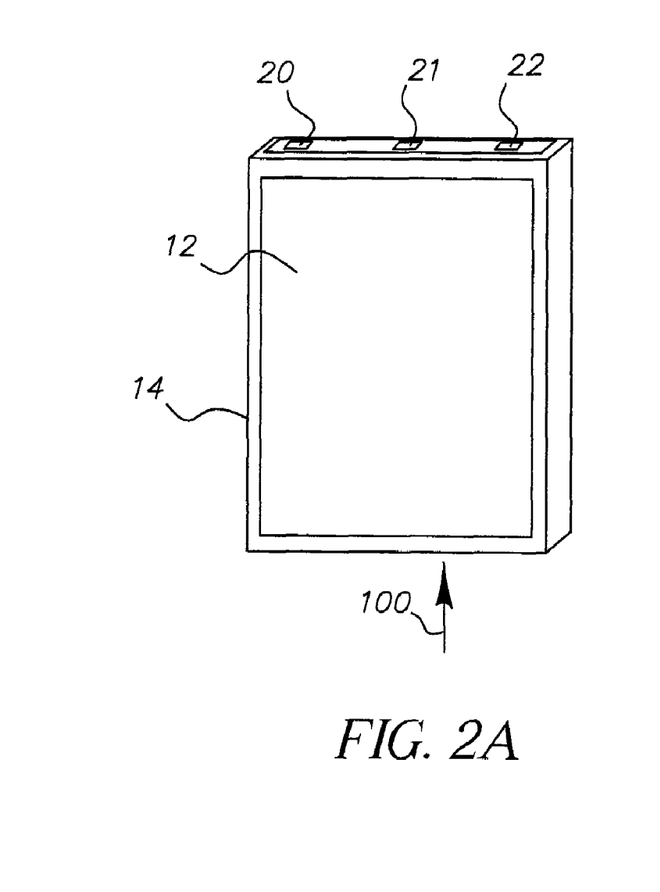
FIGS. 2A and 2B show a diagram of possible locations of the required code.
Figure 2B:
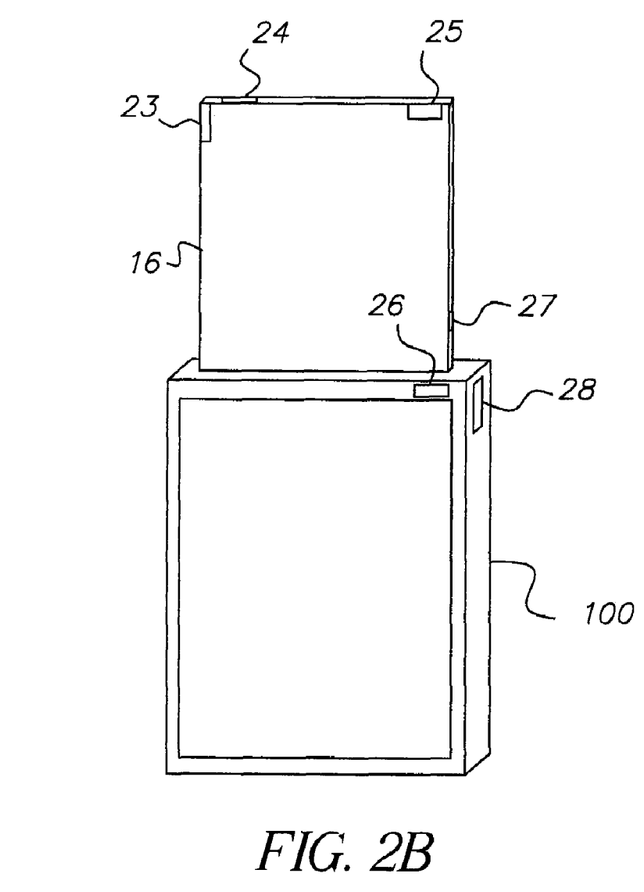

Example placements of id member 120 are shown in FIGS. 2A and 2B. Cassette 100 includes a cassette housing 12 having a frame 14. Disposed within cassette housing 12 is a phosphor material/screen 16 used to capture the latent image. As indicated above, depending on the id member employed, id member 120 can be disposed on or within cassette 100. Candidate locations of id member 120 are indicated by elements 20-28 shown in FIGS. 2A and 2B. It is noted that more than one id member can be employed with a cassette.

Figure 3A:
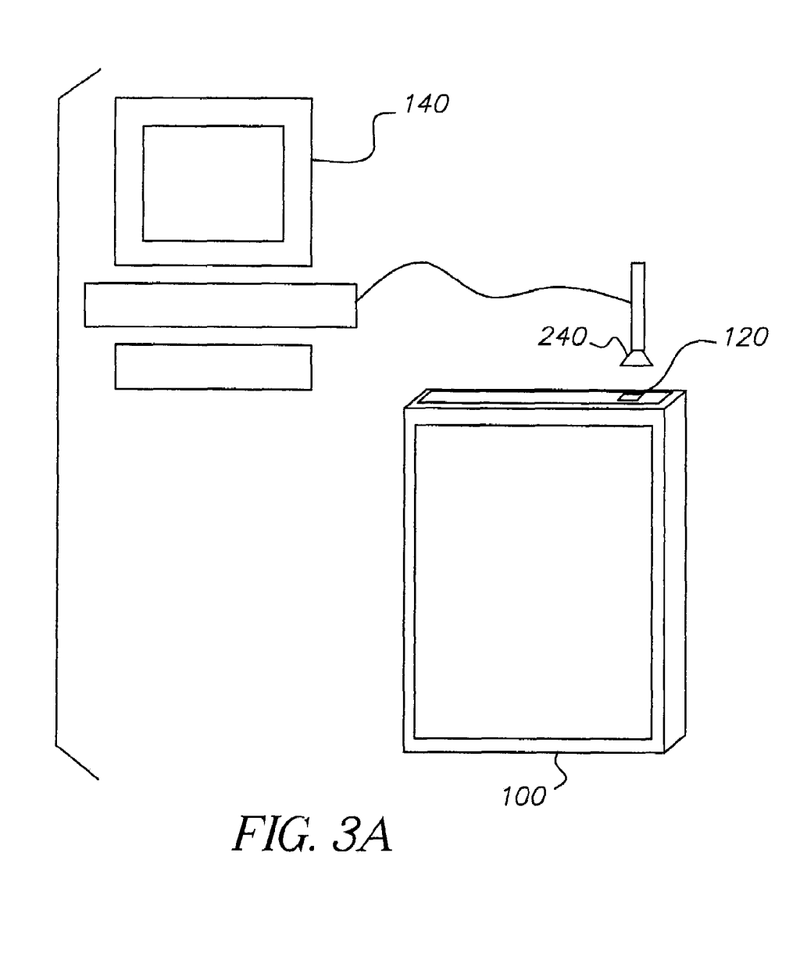
FIG. 3A shows a diagram of an exemplary programming system to set-up the scan codes.
Figure 3B:
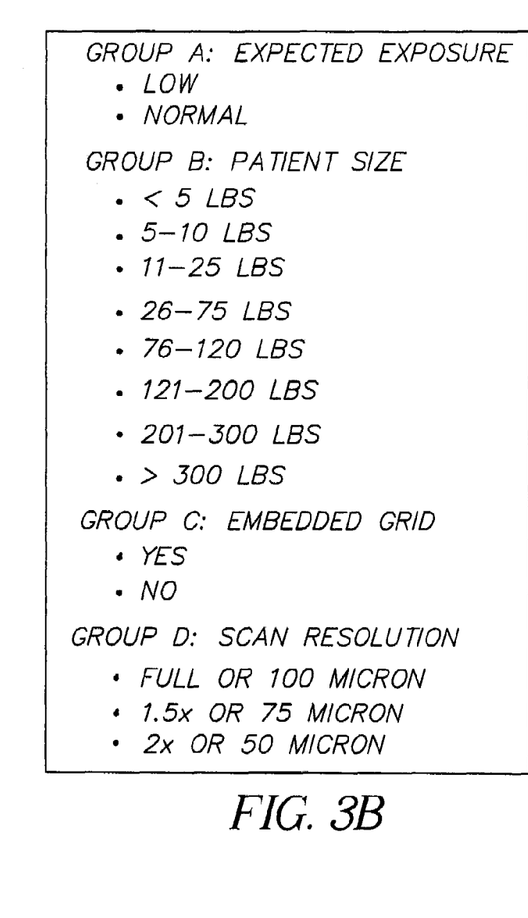
FIG. 3B shows a exemplary program options for the scan codes.

One method for programming cassette codes of id member 120 is described with reference to FIG. 3A. Cassette 100 with a programmable and scannable id member 120 is first scanned by device 240. A user interface disposed on workstation 140 allows a one time set-up, periodic or as needed configuration of one, several or all CR cassettes. Possible options that can be provided without requiring configuration are shown by Groups A through D in FIG. 3B.

Figure 4:
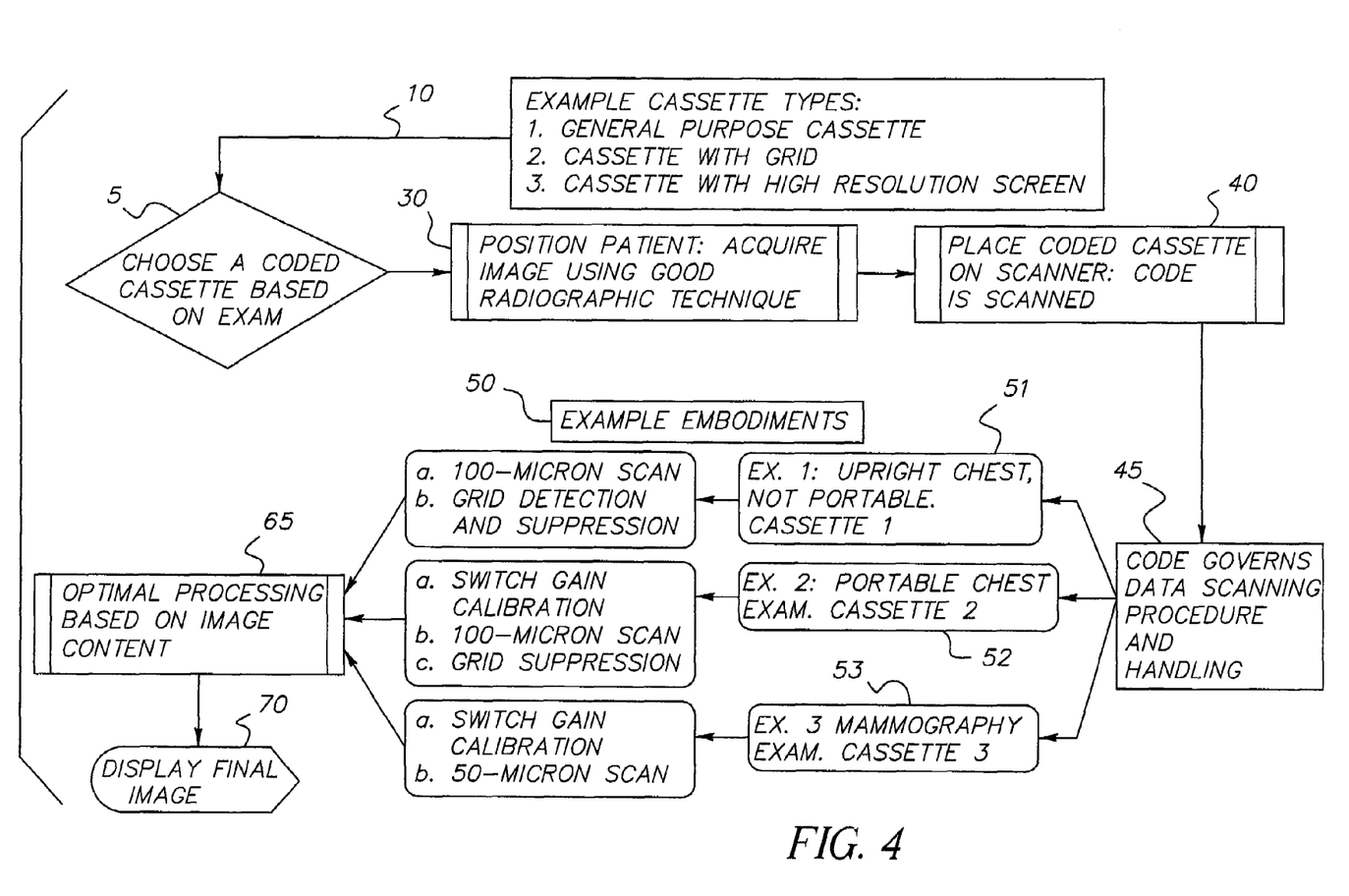
FIG. 4 shows a block diagram of an image acquisition apparatus in accordance with preferred embodiments of the present invention.

In FIG. 4 there is shown three example embodiments of the present invention.

Referring to blocks 5 and 10 of FIGS. 1 and 4, a cassette is chosen.

Example cassette types include a general-purpose cassette, a cassette with an imbedded grid, and a cassette with a high-resolution screen. Different handling is required for each cassette type, however this handling is not governed by exam information such as body part and projection. Rather, it is governed by the qualities of the cassette type. The selection of the cassette may depend on the image being acquired. For example, if a technologist is performing an upright chest exam, the technologist may choose a general-purpose cassette to perform this exam.

Using the selected cassette, the image is acquired (block 30 shown in FIGS. 1 and 4).

At block 40, device 240 is used to scan id member 120 to acquire (either directly, or indirectly through database 130), the associated cassette code. The code provides information about the scanning/handling (block 45) and/or pre-processing protocols (block 50) for reader 200 or processor 210.

Once the image is read, image processing can be conducted by processor 210 (block 65). The output image can then be transmitted, displayed a display (block 70), printed using printer 220, or archived to archive 230.

An example is now provided wherein a technologist desires to perform an upright chest exam. For such an exam, the technologist may choose a general-purpose cassette. The proper positioning and technique are provided (block 30) and the cassette is taken to device 240 for the id member to be accessed. First, the id member is scanned and the associated code is determined (either directly or indirectly). Based on the code (block 45), a scanning protocol for reader 200 will be chosen and used to scan the latent image 50 disposed within the storage phosphor. In this example, outlined as Example 1 for cassette 1 (block 51), the protocol includes scanning at 100-micron pixel resolution. Also, since there is no grid in the cassette, and either a stationary grid, reciprocating grid or no grid may be used during the exam, grid detection and suppression software would be useful, and is thus part of the protocol for Example 1 (block 51).

A second example is now described with reference to a portable chest exam. In this example, the technologist may choose cassette type 2, which is a cassette with a (preferably lightweight, possibly imbedded) grid. This cassette may be used for a portable exam (chest, abdomen, pelvis, and the like) where a grid is expected to improve image contrast and otherwise not attached to the X-ray system in the form of a stationary or reciprocating grid. The code associated with the selected cassette (obtained by scanning id member 240 disposed on the cassette) would indicate (at block 52) that a scanning protocol would include a switch to a gain calibration allowing for the exploitation of lower code value deviations in a lower exposure acquisition, a 100-micron scan and grid suppression, as the specs of the grid in the cassette are known.

A third example is now provided wherein the acquisition is a mammographic acquisition. The technologist would choose cassette 3 for this exam, which includes a high-resolution screen. This cassette could be used for an exam requiring high resolution such as fingers, wrists, ankles, mammograms, and the like. These exams also tend to require less overall exposure as the body part is small, and in the interest of dose reduction for exams where lower energy beams are required (all of the aforementioned, especially mammography) a switch to a gain calibration which allows for higher deviations between the lower code values in a lower exposure acquisition could be part of this protocol as well (block 53). The code associated with this selected cassette (by means of the id member) also indicates the scanning resolution, and in the case of a high-resolution screen, a 50-micron scan would be indicated and performed.

Figures 5A, 5B:
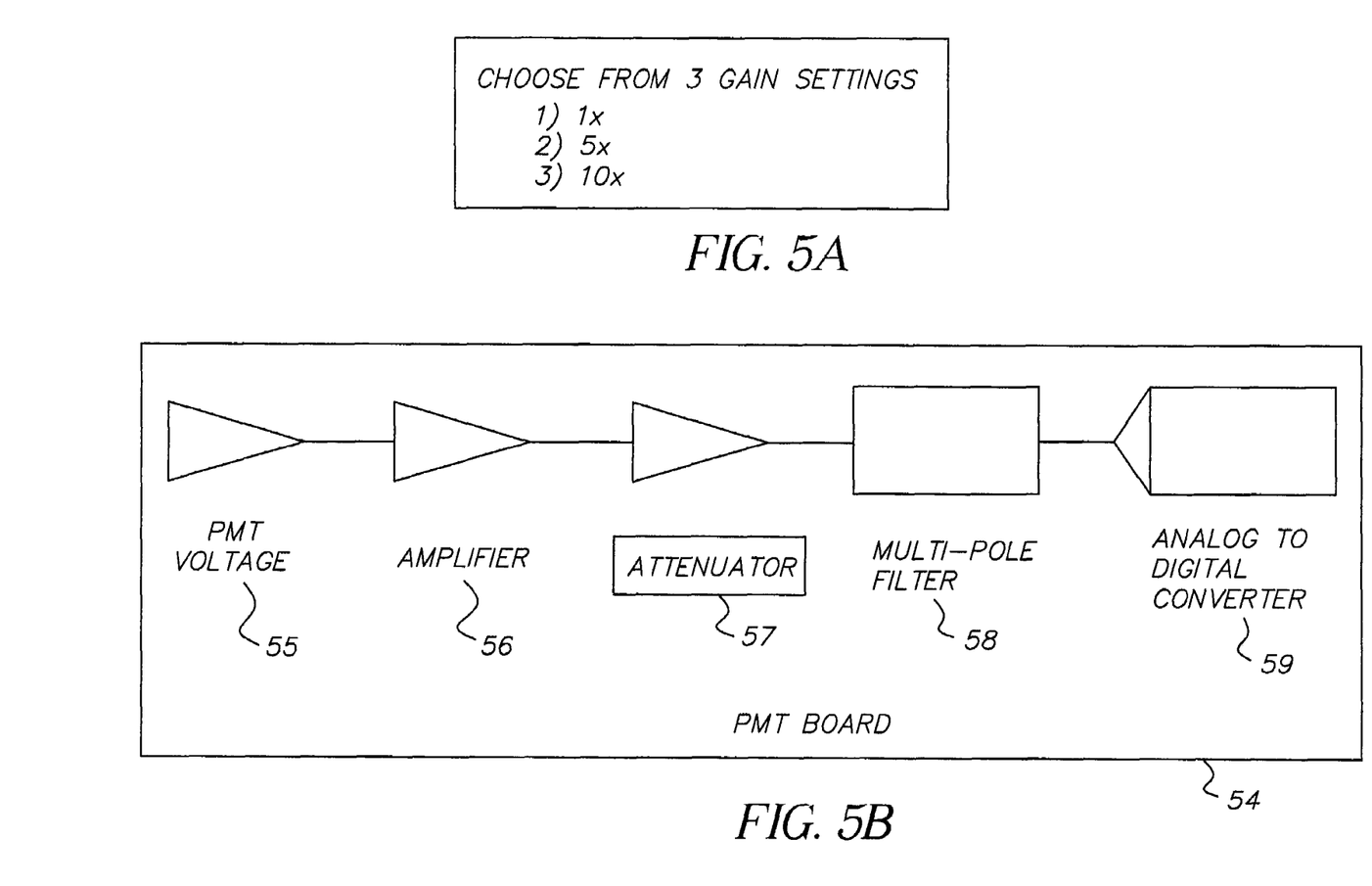
FIGS. 5A and 5B show a block diagram of the photomultiplier unit board for CR calibration.

FIGS. 5A and 5B show three examples of calibration which can be used with cassette types 2 and 3 of FIG. 4. In a CR reader, a photo multiplier board 54 supplies a high voltage 55 to a photo multiplier tube (PMT), then amplifies 56 the signal it receives from the PMT and attenuates 57 the signal depending on calibration. The signal then passes through a multi-pole filter 58 before it is sampled by an analog and digital converter 59. The multi-pole filter is made up of combinations of high pass and low pass circuits to discriminate signals based on frequency. The PMT gain can be adjusted by varying the PMT voltage and the electronic gain can be adjusted by the attenuator. For a calibration of 1× gain, it attenuates the signal only 1×. For a very low exposure, the signal to noise ratio is low. The image quality is relatively poor in such instances. When the CR is calibrated at a 5× or 10× gain, the PMT gain and/or the electronic gain increases the signal 5× or 10× above the noise floor. In such cases, when the CR cassette is exposed at very low exposure, the image quality is increased visually and the signal to noise ratio is higher. Thus, the cassette code can include information regarding the adjustment of the gain.

All further handling of the device or the image data is known to those skilled in the art and so has been previously described in available literature.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

All documents, patents, journal articles and other materials cited in the present application are hereby incorporated by reference.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A storage phosphor radiography imaging method that employs a cassette comprising a storage phosphor screen adapted to be exposed to x-rays to store a latent x-ray image in the screen and read using a reader, the method comprising the steps of:

associating cassette information with the cassette using an identification member affixed to the cassette or storage phosphor screen, the cassette information comprising information relating to characteristics of the cassette relevant to the reading of the screen by the reader;

prior to reading the exposed storage phosphor screen to generate a digital image signal, scanning the identification member to obtain the cassette information; and reading the exposed storage phosphor screen in accordance with the cassette information to generate the digital image signal.

2. The method of claim 1, wherein the cassette information further comprises information relating to characteristics of the cassette relevant to processing of the generated digital image signal, and the method further comprises the step of:

processing the digital image signal in accordance with the cassette information.

3. The method of claim 2, wherein the cassette information relates to at least one of the following:
   a type of grid;
   scanning characteristics associated with a grid used or absent from the cassette;
   laser spot size;
   laser spot shape;
   laser power;
   variable sampling clock for frequency;
   enable and disable collector profile correction for calibration;
   enable/disable recalibration;
   reload electronic gain setting without recalibration;
   variable PMT gain;
   ability to enable/disable fast scan filter;
   ability to change the DC level of the electronics signal;
   ability to turn on/off the laser for scanning;
   variable or differing galvo speed;
   variable slow scan sampling pitch;
   variable pixel size;
   variable pixel matrix size;
   exposure level;
   patient size;
   body part and/or projection;
   a grid;
   grid characteristics;
   screen characteristics;
   portability or ambulatory; and
   cassette type.

4. The method of claim 1, wherein the identification member is associated with a data stored in a digital database.

5. A storage phosphor radiography imaging method that employs a cassette comprising a storage phosphor screen adapted to be exposed to x-rays to store a latent x-ray image in the screen and read using a reader, the method comprising the steps of:
   associating cassette information with the cassette using an identification member affixed to the cassette or storage phosphor screen, the cassette information comprising information relating to characteristics of the cassette relevant to the reading of the screen by the reader;
   prior to reading the exposed storage phosphor screen to generate a digital image signal, scanning the identification member to obtain the cassette information; and
   reading the exposed storage phosphor screen in accordance with the cassette information to generate the digital image signal;
   wherein the cassette information relates to characteristics of a grid associated with the cassette.

6. A storage phosphor radiography imaging method that employs a cassette comprising a storage phosphor screen adapted to be exposed to x-rays to store a latent x-ray image in the screen and read using a reader, the method comprising the steps of:
   associating cassette information with the cassette using an identification member affixed to the cassette or storage phosphor screen, the cassette information comprising information relating to characteristics of the cassette relevant to the reading of the screen by the reader;
   prior to reading the exposed storage phosphor screen to generate a digital image signal, scanning the identification member to obtain the cassette information; and
   reading the exposed storage phosphor screen in accordance with the cassette information to generate the digital image signal;
   wherein the cassette information includes information related to a calibration of the reader.

7. The method of claim 6, wherein the calibration affects a PMT gain or electronic gain of the reader.

8. A storage phosphor radiography imaging method that employs a cassette comprising a storage phosphor screen adapted to be exposed to x-rays to store a latent x-ray image in the screen, the method comprising the steps of:
   providing the cassette holding a storage phosphor screen, the cassette including an identification member affixed thereto wherein cassette code information is associated with the identification member;
   providing a scanning member adapted to scan the identification member to obtain the cassette code information prior to reading the exposed storage phosphor screen to generate an digital image signal;
   converting the cassette code information to a reading procedure; and
   reading the exposed storage phosphor screen in accordance with the reading procedure to generate the digital image signal.

9. The method of claim 8, wherein the cassette code information includes information related to a calibration of a reader adapted to read the exposed storage phosphor screen to generate the digital image signal.

10. The method of claim 9, wherein the calibration affects a PMT gain or electronic gain of the reader.

11. A storage phosphor radiography imaging method that employs a cassette comprising a storage phosphor screen adapted to be exposed to x-rays to store a latent x-ray image in the screen, the method comprising the steps of:
   providing the cassette comprising the screen, the cassette including an identification member affixed thereto wherein cassette code information is associated with the identification member, the cassette code information comprising information relating to characteristics of the cassette relevant to reading of the screen by a reader to generate a digital image signal and comprising characteristics of the cassette relevant to processing of the generated digital image signal;
   providing a scanning member adapted to scan the identification member to obtain the cassette code information;
   after obtaining the cassette code information, reading the exposed storage phosphor screen by the reader in accordance with the cassette code information to generate the digital image signal; and
   processing the digital image signal in accordance with the cassette code information.

12. A storage phosphor radiography imaging method that employs a cassette comprising a storage phosphor screen adapted to be exposed to x-rays to store a latent x-ray image in the screen, the method comprising the steps of:
   providing the cassette comprising the screen, the cassette including an identification member affixed thereto wherein cassette code information is associated with the identification member, the cassette code information comprising information relating to characteristics of the cassette relevant to reading of the screen by a reader to generate a digital image signal and comprising characteristics of the cassette relevant to processing of the generated digital image signal;
   providing a scanning member adapted to scan the identification member to obtain the cassette code information;
   after obtaining the cassette code information, reading the exposed storage phosphor screen by the reader in accordance with the cassette code information to generate the digital image signal; and processing the digital image signal in accordance with the cassette code information;

wherein the cassette code information includes information related to a calibration of the reader.

13. The method of claim 12, wherein the calibration affects a PMT gain or electronic gain of the reader.

* * * * *